(12) United States Patent
Chang et al.

(10) Patent No.: US 11,815,520 B2
(45) Date of Patent: Nov. 14, 2023

(54) MOVABLE APPARATUS FOR COLLECTING AND ANALYZING SPECIMENS

(71) Applicant: Biot Korea Inc., Gwangju (KR)

(72) Inventors: Yeong Jun Chang, Seoul (KR); Jung Min Lee, Seoul (KR)

(73) Assignee: Biot Korea Inc., Gwangju (KR)

( * ) Notice: Subject to any disclaimer, the term of this patent is extended or adjusted under 35 U.S.C. 154(b) by 308 days.

(21) Appl. No.: 17/369,464

(22) Filed: Jul. 7, 2021

(65) Prior Publication Data
US 2022/0011334 A1 Jan. 13, 2022

(30) Foreign Application Priority Data
Jul. 10, 2020 (KR) ........................ 10-2020-0085458

(51) Int. Cl.
| | | |
|---|---|---|
| *C12N 15/10* | (2006.01) | |
| *B01L 3/00* | (2006.01) | |
| *G01N 35/10* | (2006.01) | |
| *B01L 3/02* | (2006.01) | |
| *G01N 35/04* | (2006.01) | |
| *G01N 35/00* | (2006.01) | |

(52) U.S. Cl.
CPC ....... *G01N 35/04* (2013.01); *G01N 35/00871* (2013.01); *G01N 2035/0401* (2013.01)

(58) Field of Classification Search
CPC ............. G01N 35/04; G01N 35/00871; G01N 2035/0401; G01N 35/0099; G01N 33/56983; G01N 35/02; A61B 90/361; A61B 2010/0216; A61B 10/02; A61B 10/0045; A61B 5/08; A61B 10/0051; A61G 10/005; A61G 10/023; A61L 2/10; A61L 2/18; B60P 3/00; F24F 7/06; F24F 11/0001; F24F 2011/0005

See application file for complete search history.

(56) References Cited

U.S. PATENT DOCUMENTS

2017/0087725 A1\* 3/2017 Neishaboori ............ B25J 11/00

FOREIGN PATENT DOCUMENTS

KR 10-2014-0029959 A 3/2014

\* cited by examiner

*Primary Examiner* — Jennifer Wecker
*Assistant Examiner* — Oyeleye Alexander Alabi
(74) *Attorney, Agent, or Firm* — Knobbe, Martens, Olson & Bear, LLP (57) ABSTRACT

This application relates to a movable apparatus for collecting and analyzing specimens. In one aspect, the movable apparatus includes a transport means configured to be moved independently and to maintain negative pressure therein by a negative pressure module, and a specimen collecting device arranged in the transport means and configured to collect a specimen under remote control by inserting a specimen collecting member into the nasal cavity of a testee who enters the transport means. The apparatus may also include a specimen transport device arranged in the transport means and configured to transport the specimen collecting member under remote control that has collected the specimen in one direction, and a specimen analysis device arranged in the transport means and configured to extract the specimen from the specimen collecting member that has been transported by the specimen transport device under remote control and to analyze the specimen.

8 Claims, 7 Drawing Sheets

MOVABLE APPARATUS FOR COLLECTING AND ANALYZING SPECIMENS

CROSS REFERENCE TO RELATED APPLICATION

The present application claims priority to Korean Patent Application No. 10-2020-0085458, filed Jul. 10, 2020, the entire contents of which is incorporated herein for all purposes by this reference.

BACKGROUND

Technical Field

The present disclosure relates generally to a movable apparatus for collecting and analyzing specimens and, more particularly, to a movable apparatus for collecting and analyzing specimens capable of being moved to perform specimen collection and analysis in various places, capable of performing the specimen collection and analysis without direct contact with a testee to prevent further infection due to direct contact with the testee, and capable of performing the specimen collection and analysis in negative pressure environment to prevent further infection due to the release of pathogens.

DESCRIPTION OF THE RELATED TECHNOLOGY

Recently, respiratory diseases caused by bacterial or viral infections have rapidly increased.

Bacteria or viruses are easily transmitted between people through droplets from patients, so widespread further infection may occur and lead to epidemics of respiratory diseases.

Therefore, it is necessary to quickly select and isolate patients with respiratory diseases at the early stage of an outbreak of a respiratory disease.

SUMMARY

The present disclosure has been made keeping in mind the above problems occurring in the related art, and the present disclosure is intended to provide a movable apparatus for collecting and analyzing specimens, wherein the apparatus is configured to be movable to perform specimen collection and analysis in various places, the specimen collection and analysis are performed without direct contact with a testee to prevent further infection due to direction contact with the testee, and the specimen collection and analysis are performed in negative pressure environment to prevent further infection due to the release of pathogens.

In order to accomplish the above objective, a movable apparatus for collecting and analyzing specimens according to the present disclosure includes: a transport means configured to be moved independently and to maintain negative pressure therein by a negative pressure module; a specimen collecting device arranged in the transport means and configured to collect a specimen under remote control by inserting a specimen collecting member into a nasal cavity of a testee who enters the transport means; a specimen transport device arranged in the transport means and configured to transport the specimen collecting member under remote control that has collected the specimen in one direction; and a specimen analysis device arranged in the transport means and configured to extract the specimen from the specimen collecting member that has been transported by the specimen transport device under remote control and to analyze the specimen.

The transport means may be an automobile in which wheels may be rotated by power of a motor.

The transport means may include: a video capturing module configured to capture a video of a face of the testee; and a communication module configured to transmit a video signal of the video capturing module in real time.

The transport means may include a disinfection module configured to spray disinfectant or to radiate UV rays into the transport means.

The negative pressure module may include: a suction fan configured to suction air in the transport means; and a filter configured to filter foreign substances from the air in the transport means and air supplied into the transport means.

The specimen collecting device may include: an arm configured to be moved in every direction (forward, rearward, leftward, rightward, upward, and downward) by operation of a drive means; and a holder arranged on an end of the arm and configured to hold and lock the specimen collecting member by the operation of the drive means.

The specimen transport device may include: a conveyor configured to be rotated by operation of a drive means and including a tube support supporting a tube containing the specimen collecting member therein.

The specimen transport device may include: a gripper configured to grip the tube containing the specimen collecting member therein and to insert the tube into the specimen analysis device.

As described above, the movable apparatus for collecting and analyzing specimens of the present disclosure includes the transport means. Accordingly, the specimen collecting device, the specimen transport device, and the specimen analysis device may be moved by the transport means, so that the specimen collection and analysis can be performed in various places.

The movable apparatus for collecting and analyzing specimens of the present disclosure includes the transport means with the negative pressure module. Accordingly, the transport means may maintain negative pressure therein by the negative pressure module to prevent the release of pathogens during a process of the specimen collection and analysis, so that further infection due to the release of pathogens can be prevented.

The movable apparatus for collecting and analyzing specimens of the present disclosure includes the specimen collecting device, the specimen transport device, and the specimen analysis device operated under remote control. Accordingly, direct contact with the testee during the process of the specimen collection and analysis is prevented, so that further infection due to direct contact with the testee can be prevented.

BRIEF DESCRIPTION OF THE DRAWINGS

The above and other objectives, features, and other advantages of the present disclosure will be more clearly understood from the following detailed description when taken in conjunction with the accompanying drawings.

DETAILED DESCRIPTION

Determination of whether a testee has a respiratory disease may be performed by a manual collecting method of inserting a cotton swab into the nasal cavity of the testee or by a specimen collecting device, and then the collected specimen is analyzed by various specimen analysis devices such as a specimen analysis apparatus disclosed in Korean Patent Application Publication No. 10-2014-0029959.

However, specimen collection and analysis for the determination of respiratory diseases should be performed in a place equipped with a specimen collecting device and a specimen analysis device, such as a hospital. Therefore, the testee must find and visit the place because of limitation in place of specimen collection and analysis.

Furthermore, when specimen collection and analysis for the determination of respiratory diseases are performed in a general hospital, direct contact between a medical staff and the testee and direct contact between the public and the testee may occur, so there is a problem of further infection due to the direct contact with the testee.

Furthermore, the release of pathogens occurs during a process of the specimen collection and analysis for the determination of respiratory diseases, so there is a problem of further infection due to the release of pathogens even when the medical staff or the public do not have direct contact with the testee.

Although the medical staff wears protective gear to prevent infection, the user's fatigue is aggravated because the movement is inconvenient when the medical staff wear the protective gear and the provision of the protective gear incurs significant costs.

For the above mentioned reasons, the relevant field of the present disclosure attempts development of an apparatus for collecting and analyzing specimens, which is movable to perform the specimen collection and analysis in various places, to perform the specimen collection and analysis without direct contact with the testee to prevent further infection due to direct contact with the testee, and to perform the specimen collection and analysis in negative pressure environment to prevent further infection due to the release of pathogens. However, so far, no satisfactory results have been obtained.

Hereinbelow, the present disclosure will be described in detail with reference to accompanying drawings.

Figure 1:
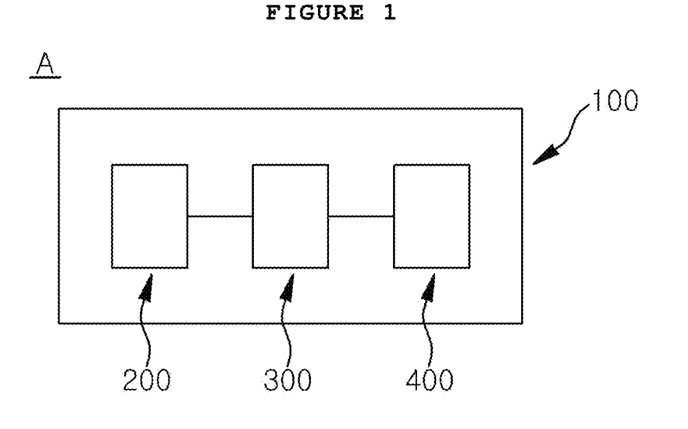
FIG. 1 is a schematic view showing the structure of a movable apparatus for collecting and analyzing specimens according to the present disclosure.

As shown in FIG. 1, a movable apparatus for collecting and analyzing specimens A according to the present disclosure includes: a transport means 100: a specimen collecting device 200; a specimen transport device 300; and a specimen analysis device 400.

The transport means 100 of the present disclosure is moved independently, and negative pressure therein is maintained by a negative pressure module 110.

The specimen collecting device 200, the specimen transport device 300, and the specimen analysis device 400 arranged in the transport means 100 are moved as the transport means 100 is moved. Accordingly, specimen collection and analysis are performed in various places and the release of pathogens during a process of the specimen collection and analysis is prevented by maintenance of negative pressure in the transport means 100.

Figure 3:
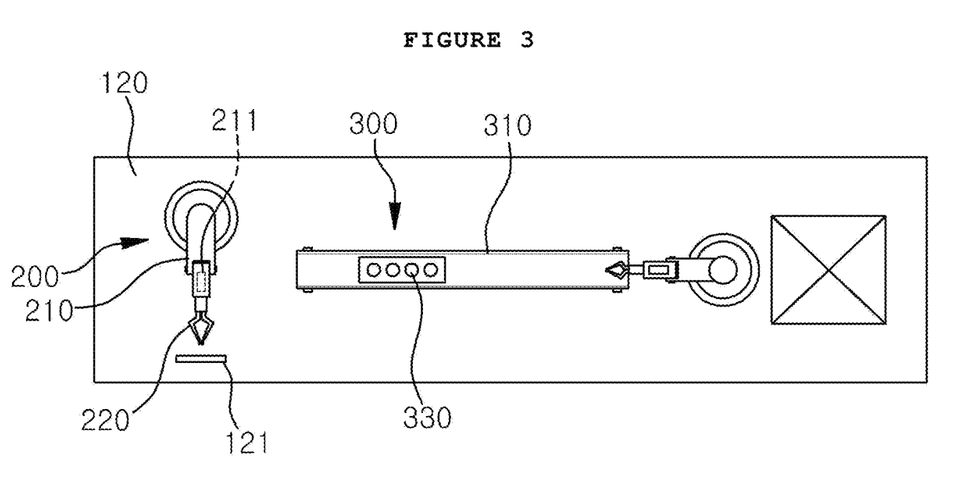
FIG. 3 is an example view showing a form of arrangement of a specimen collecting device, a specimen transport device, and a specimen analysis device in the movable apparatus for collecting and analyzing specimens according to the present disclosure.

The transport means 100 includes a support 120, and the support 120 stably supports the specimen collecting device 200, the specimen transport device 300, and the specimen analysis device 400 as shown in FIG. 3.

The support 120 includes a face holder 121. As the face of the testee is placed on the face holder 121, a location of the face of the testee may remain constant.

The transport means 100 may include: a video capturing module 130 configured to capture a video of the face of the testee; and a communication module 140 configured to transmit a video signal of the video capturing module 130 in real time. Therefore, a medical staff may check the face of the testee by a remote control operation at a remote control place, for example, by the video transmitted by the communication module 140, so that the specimen collection under remote control may be efficiently performed.

The transport means 100 includes a disinfection module 150 spraying disinfectant therein or radiating UV rays thereinto. Before or after the specimen collection and analysis, the disinfection module 150 sprays the disinfectant or radiates the UV rays into the transport means 100, so that the inside of the transport means 100 may be disinfected.

Figure 4:
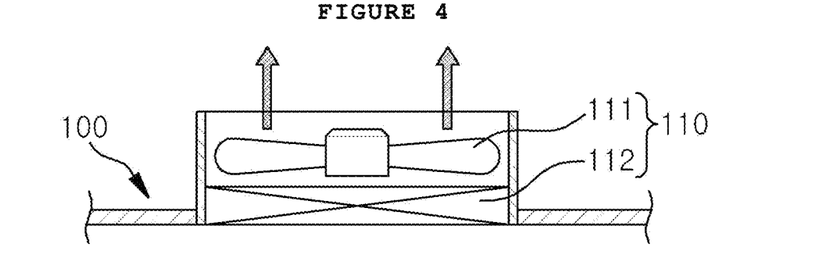
FIG. 4 is an example view showing the structure of a negative pressure module of the transport means in the movable apparatus for collecting and analyzing specimens according to the present disclosure.

As shown in FIG. 4, the negative pressure module 110 of the transport means 100 includes: a suction fan 111 suctioning air in the transport means 100; and a filter 112 filtering foreign substances from the air in the transport means 100 or air supplied into the transport means 100. The suction fan 111 and the filter 112 maintain negative pressure in the transport means 100 to prevent the release of pathogens.

Figure 2:
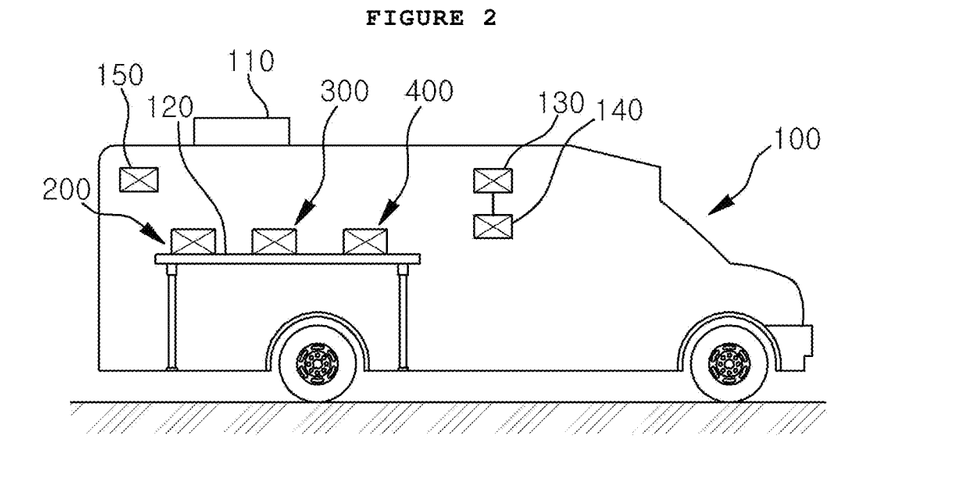
FIG. 2 is an example view showing an embodiment of a transport means of the movable apparatus for collecting and analyzing specimens according to the present disclosure.

Meanwhile, the transport means 100 may have any conventional structure and method if the structure and method allow the transport means 100 to be moved independently and store the specimen collecting device 200, the specimen transport device 300, and the specimen analysis device 400 therein. As an example, the transport means 100 may be an automobile in which wheels are rotated by power of a motor as shown in FIG. 2.

The specimen collecting device 200 of the present disclosure is arranged in the transport means 100. The specimen collecting device 200 collects a specimen by inserting a specimen collecting member C into the nasal cavity of the testee who enters the transport means 100 under remote control.

Accordingly, the specimen collecting device 200 performs the specimen collection without direct contact between the medical staff and the testee.

Figure 5:
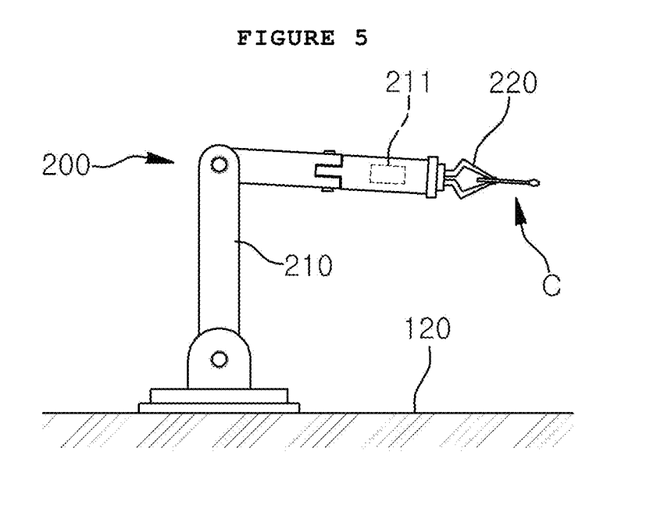
FIG. 5 is an example view showing the structure of the specimen collecting device in the movable apparatus for collecting and analyzing specimens according to the present disclosure.

The specimen collecting device 200 includes: an arm 210 moved in every direction (forward, rearward, leftward, rightward, upward, and downward) by the operation of a drive means (not shown); and a holder 220 arranged on an end of the arm 210 and holding and locking the specimen collecting member C by the operation of the drive means (not shown). The arm 210 and the holder 220 are operated to insert the specimen collecting member C into the nasal cavity of the testee, thus achieving the specimen collection.

The arm 210 includes a plurality of joints (not indicated with reference numeral), so movement in the every direction of the arm may be efficiently moved by the joints.

Furthermore, the arm 210 includes a pressure detection member 211 detecting pressure affecting the specimen collecting member C during the specimen collection. Therefore, when the specimen collecting member C is inserted into the nasal cavity of the testee, the pressure detected by the pressure detection member 211 may be maintained within a predetermined range, so that the specimen collecting member C may reach the mucous membrane precisely and the testee may avoid excessive insertion of the specimen collecting member C.

The pressure detection member 211 may have any conventional structure or method if the structure or method allows the pressure detection member 211 to efficiently detect pressure affecting the specimen collecting member C, and a detailed description of the pressure detection member 211 will be omitted.

The specimen collecting device 200 includes a cutting module (not shown). After the specimen collection, the cutting module may partially cut the specimen collecting member C and, specifically, may cut a portion of the specimen collecting member C other than a head thereof.

Meanwhile, remote control may be performed in a space that is a separately partitioned portion in the transport means 100.

A remote control operator may be in the separate-partitioned space in the transport means 100 and perform remote control while by identify the testee through a transparent window.

Remote control may be performed in a place outside the transport means 100.

In this case, remote control operator may be in the place outside the transport means 100 and perform remote control by checking the video, which is made by the video capturing module 130 provided in the transport means 100, through a monitor in real time.

The specimen transport device 300 of the present disclosure is arranged in the transport means 100 and transports the specimen collecting member C that has collected the specimen in one direction under remote control.

Therefore, the specimen transport device 300 allows the specimen collecting member C to be transported without medical staff contact.

Figure 7:
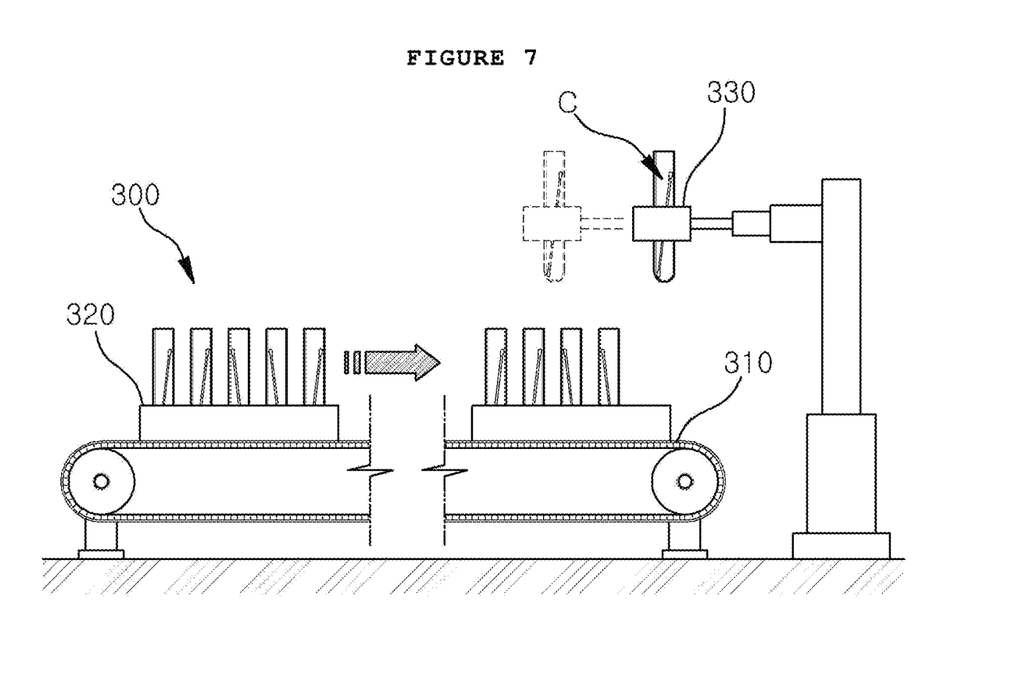
FIG. 7 is an example view showing transportation of the specimen collecting member performed by the specimen transport device in the movable apparatus for collecting and analyzing specimens according to the present disclosure.

The specimen transport device 300 includes a conveyor 310. The conveyor 310 is rotated by the operation of the drive means (not shown) and on which a tube support 320 supporting a tube (not indicated with reference numeral) containing the specimen collecting member C is placed. The tube containing the specimen collecting member C is held in the tube support 320, so that the specimen collecting member C may be stably transported.

The specimen transport device 300 may include a gripper 330 gripping the tube containing the specimen collecting member C and inserting the tube into the specimen analysis device 400. The gripper 330 may allow the specimen collecting member C to be stably inserted into the specimen analysis device 400.

The specimen analysis device 400 of the present disclosure is arranged in the transport means 100. The specimen analysis device 400 extracts the specimen from the specimen collecting member C transported by the specimen transport device 300 under remote control and analyzes the specimen.

Accordingly, the medical staff checks an analysis result of the specimen analysis device 400, and thus it is determined whether the testee is infected with a pathogen.

Meanwhile, the specimen analysis device 400 may be any conventional structure and method if the structure and method analyze the specimen from the specimen collecting member C transported by the specimen transport device 300. As an example, the specimen analysis device 400 may be a polymerase chain reaction (PCR) analyzer including a preprocessing module (not shown) preprocessing the specimen.

The preprocessing module divides the specimen into a plurality of columns and centrifuges or vacuums the columns, so that a genetic material obtained in the preprocessing process may be input into the PCR analyzer 400.

The specimen collection and analysis performed by the movable apparatus for collecting and analyzing specimens A according to the present disclosure will be describe in detail as follows.

According to the present disclosure, the specimen collecting device 200 is arranged in the transport means 100.

Therefore, when the specimen collecting device 200 is operated under remote control after the testee enters the inside of the transport means 100 and stands in front of the specimen collecting device 200, the specimen collection is performed without direct contact between the medical staff and the testee.

Figure 6:
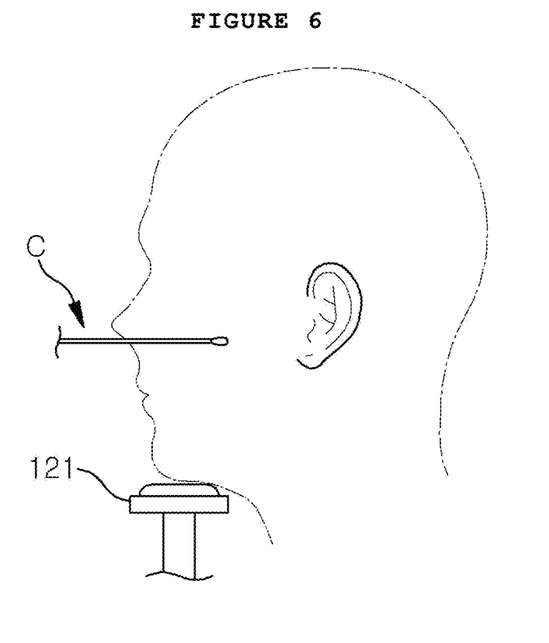
FIG. 6 is an example view showing specimen collection performed by the specimen collecting device in the movable apparatus for collecting and analyzing specimens according to the present disclosure.

The specimen collecting device 200 includes: the arm 210 moved in the every direction (forward, rearward, leftward, rightward, upward, and downward) by the operation of the drive means; and the holder 220 arranged at the end of the arm 210 and holding and locking the specimen collecting member C by the operation of the drive means, as shown in FIG. 5. The arm 210 and the holder 220 are operated to insert the specimen collecting member C into the nasal cavity of the testee to achieve the specimen collection, as shown in FIG. 6.

However, depending on a location of the face of the testee, it is difficult to collect the specimen by the specimen collecting device 200.

For example, when the face of the testee is located in a portion separated from the front of the specimen collecting device 200, the arm 210 and the holder 220 may not reach the face of the testee, so it may be difficult to perform the specimen collection through the specimen collecting device 200.

However, since the transport means 100 of the present disclosure includes the support 120 supporting the specimen collecting device 200, the specimen transport device 300, and the specimen analysis device 400, and the support 120 includes the face holder 121, when the testee places the face of the testee on the face holder 121, a location of the face of the test may be located in front of the specimen collecting device 200 precisely and the specimen collection through the specimen collecting device 200 may be efficiently performed.

Meanwhile, the specimen collecting device 200 of the present disclosure may include the cutting module (not shown). Therefore, after the specimen collection, the cutting module may cut a portion of the specimen collecting member C other than the head thereof.

The specimen transport device 300 is arranged in the transport means 100 of the present disclosure.

Accordingly, the specimen transport device 300 is operated under remote control, so that the specimen collecting member C that has collected the specimen is transported without medical staff contact.

Before the operation of the specimen transport device 300, the specimen collecting member C gripped by the specimen collecting device 200 is held in the specimen transport device 300 by operations of the arm 210 and the holder 220 of the specimen collecting device 200.

The specimen transport device 300 is rotated by the operation of the drive means and includes the conveyor 310 on which the tube support 320 supporting the tube (not indicated with reference numeral) containing the specimen collecting member C. As shown in FIG. 7, when the tube containing the specimen collecting member C is held in the tube support 320, the specimen collecting member C is stably transported.

Furthermore, the specimen transport device 300 may include the gripper 330 gripping the tube containing the specimen collecting member C and inserting the tube into the specimen analysis device 400. After the transportation of the specimen collecting member C by the conveyor 310, the specimen collecting member C may be stably inserted into the specimen analysis device 400 by the gripper 330.

The specimen analysis device 400 is arranged in the transport means 100 of the present disclosure.

After the insertion of the specimen collecting member C into the specimen analysis device 400, the specimen analysis device 400 is operated under remote control to perform the analysis of the specimen extracted from the specimen collecting member C without medical staff contact. Accordingly, it is accurately determined whether the testee is infected or not by a result of the specimen analysis of the specimen analysis device 400.

The specimen analysis device 400 may be the PCR analyzer including the preprocessing module (not shown) preprocessing the specimen. When the preprocessing module divides the specimen into the plurality of columns and then centrifuges or vacuums the columns the columns to obtain a genetic material, the genetic material obtained by the preprocessing is inserted into the PCR analyzer 400, thereby achieving the specimen analysis.

Meanwhile, the transport means 100 of the present disclosure is moved independently, so the specimen collecting device 200, the specimen transport device 300, and the specimen analysis device 400 provided in the transport means 100 are moved as the transport means 100 of the present disclosure is moved, so the apparatus of the present disclosure can perform the specimen collection and analysis in various places.

The transport means 100 of the present disclosure maintains negative pressure therein by the negative pressure module 110 to prevent the release of pathogens outflow during the process of specimen collection and analysis, so further infection due to the release of pathogens may be prevented.

The transport means 100 of the present disclosure includes: the video capturing module 130 configured to capture a video of the face of the testee; and the communication module 140 configured to transmit a video signal of the video capturing module 130 in real time. Therefore, a remote control operator located at a long-distance place, i.e., a medical staff may check the face of the testee from the video, whereby the specimen collection by remote control may be precisely performed.

The specimen collecting member C may be precisely inserted into the nasal cavity of the testee under remote control while the remote control operator checks the face of the testee through the video, so that the specimen collection may be precisely performed.

Furthermore, the transport means 100 may include the disinfection module 150 spraying disinfectant or radiating UV rays into the transport means 100, whereby the inside of the transport means 100 may be disinfected by the disinfection module 150 spraying disinfectant or radiating UV rays after and before the specimen collection and analysis.

Although a preferred embodiment of the present disclosure has been described for illustrative purposes, those skilled in the art will appreciate that various modifications, additions and substitutions are possible, without departing from the scope and spirit of the present disclosure as disclosed in the accompanying claims.

What is claimed is:

1. A movable apparatus for collecting and analyzing specimens, the apparatus comprising:
   transport means configured to be moved independently and to maintain negative pressure therein by a negative pressure module;
   a specimen collecting device arranged in the transport means and configured to collect a specimen under remote control by inserting a specimen collecting member into a nasal cavity of a testee who enters the transport means;
   a specimen transport device arranged in the transport means and configured to transport the specimen collecting member under remote control that has collected the specimen in one direction; and
   a specimen analysis device arranged in the transport means and configured to extract the specimen from the specimen collecting member that has been transported by the specimen transport device under remote control and to analyze the specimen.

2. The movable apparatus of claim 1, wherein the transport means comprises an automobile in which wheels are rotated by power of a motor.

3. The movable apparatus of claim 1, wherein the transport means further comprises:
   a video capturing module configured to capture a video of a face of the testee; and
   a communication module configured to transmit a video signal of the video capturing module in real time.

4. The movable apparatus of claim 1, wherein the transport means further comprises a disinfection module configured to spray disinfectant or to radiate UV rays into the transport means.

5. The movable apparatus of claim 1, wherein the negative pressure module comprises:
   a suction fan configured to suction air in the transport means; and
   a filter configured to filter foreign substances from the air in the transport means and air supplied into the transport means.

6. The movable apparatus of claim 1, wherein the specimen collecting device comprises:
   an arm configured to be moved in every direction, including forward, rearward, leftward, rightward, upward, and downward directions, by operation of drive means; and
   a holder arranged on an end of the arm and configured to hold and lock the specimen collecting member by the operation of the drive means.

7. The movable apparatus of claim 1, wherein the specimen transport device comprises:

a conveyor configured to be rotated by operation of drive means and comprising a tube support supporting a tube containing the specimen collecting member therein.

8. The movable apparatus of claim 7, wherein the specimen transport device comprises:

a gripper configured to grip the tube containing the specimen collecting member therein and to insert the tube into the specimen analysis device.

* * * * *